(12) United States Patent
Gordon

(10) Patent No.: US 6,188,745 B1
(45) Date of Patent: Feb. 13, 2001

(54) CT SCANNER COMPRISING A SPATIALLY ENCODED DETECTOR ARRAY ARRANGEMENT AND METHOD

(75) Inventor: Bernard M. Gordon, Manchester-by-the-Sea, MA (US)

(73) Assignee: Analogic Corporation, Peabody, MA (US)

(*) Notice: Under 35 U.S.C. 154(b), the term of this patent shall be extended for 0 days.

(21) Appl. No.: 09/159,067

(22) Filed: Sep. 23, 1998

(51) Int. Cl.⁷ .................................................. A61B 6/03
(52) U.S. Cl. .................................................. 378/19; 378/15
(58) Field of Search .................................. 378/4, 19, 15, 378/147, 150

(56) References Cited

U.S. PATENT DOCUMENTS

| | | | |
|---|---|---|---|
| 5,262,946 | 11/1993 | Heuscher | 364/413.18 |
| 5,291,402 | 3/1994 | Pfoh | 364/413.14 |
| 5,355,309 | * 10/1994 | Eberhard et al. | 378/19 |
| 5,390,226 | 2/1995 | Tam | 378/19 |
| 5,510,622 | 4/1996 | Hu et al. | 250/367 |
| 5,668,851 | 9/1997 | Dobbs | 378/19 |
| 5,717,732 | * 2/1998 | Tam | 378/4 |
| 5,757,878 | 5/1998 | Dobbs et al. | 378/19 |
| 5,781,606 | 7/1998 | Dobbs et al. | 378/19 |
| 5,818,897 | 10/1998 | Gordon | 378/19 |

FOREIGN PATENT DOCUMENTS

| | | |
|---|---|---|
| 0 715 830 A1 | 6/1996 | (EP) . |
| 6-169912 | * 6/1994 | (JP) .................... 378/19 |

OTHER PUBLICATIONS

Brochure: Toshiba Introduces New Generation CT—Multi-slice Helical CT, CAR '98, Tokyo, Jun. 24–27, 1998.

* cited by examiner

Primary Examiner—David P. Porta
(74) Attorney, Agent, or Firm—McDermott, Will & Emery

(57) ABSTRACT

A CT scanner comprising a spatially encoded detector arrangement for providing data values representing variable thickness slices, and a method of efficiently detecting X-rays for variable thickness slices of a CT scanner are disclosed. The spatially encoded detector arrangement includes a plurality of columns of detector elements, with the detector elements of each column being distributed and arranged so that the lengths of at least some of the detector elements of each of the columns vary in accordance with a predetermined sequence code that represents all of the whole integer values in equal increments from 1 to N, wherein N is a whole integer greater than 1, and preferably greater than 3. Preferably, the sequence code is a biquinary code of 5, 2, 2, 1 so that N is at least 10. The detector arrangement is preferably a 2D array having rows of two or more lengths so that beams of various thicknesses each can be projected onto a row or rows of detector elements having a detection area substantially matched to the corresponding beam. The spatial encoding using the sequence code preferably also allows for one or more sets of multiple slices of equal thickness to be simultaneously generated. By spatially encoding the array with the sequence code, the number of detector elements can be reduced from an array made of detector elements of equal length, i.e., the number of detector elements of each column representing the code is less than N, and more efficient X-ray conversion achieved.

10 Claims, 6 Drawing Sheets

CT SCANNER COMPRISING A SPATIALLY ENCODED DETECTOR ARRAY ARRANGEMENT AND METHOD

CROSS-REFERENCE TO RELATED APPLICATIONS

Not Applicable.

STATEMENT REGARDING FEDERALLY SPONSORED RESEARCH

Not Applicable.

REFERENCE TO MICROFICHE APPENDIX

Not Applicable.

FIELD OF THE INVENTION

The present invention relates generally to computed tomography (CT) systems and methods, and more particularly to a CT scanner comprising a spatially encoded detector arrangement for generating data values representative of variable thickness and/or multiple CT slices, and a method of efficiently detecting X-rays for variable thickness and/or multiple slices in a CT scanner.

BACKGROUND OF THE INVENTION

CT scanners of the third generation type generally comprise a source of X-rays and a detector array, both mounted on a rotatable disk or platform at diametrically opposite sides of the opening through which the scanned object is placed. During a scan the source and detectors rotate about the rotation axis, usually referred to as the Z-axis; and at precise angles of the source and detectors, data values are acquired. The data values are representative of the X-ray photons generated by the source and projected onto and sensed by the detectors at each angle so as to provide projection views corresponding to these angles of view. Some of the X-ray photons are absorbed by the object and the data values are thus a function of the integral of the density of the portion of the object through which the measured X-rays pass for each projection view measuring interval, i.e., the smaller the reading the more X-ray photons absorbed during that time interval, and thus the integral of the mass is more dense along the X-ray path. The field of view or reconstruction circle (i.e., the spatial area through which X-rays measurements are made) is typically defined by the beam angle (the angle of divergence of the beam as it is projected from a focal spot of the X-ray source to the detectors), and the distance the focal spot of the source is placed from the isocenter (the mechanical center of rotation) of the machine.

The detector array is traditionally constructed so that the detectors lie on the circumference of a circle having a center of curvature at the location where the X-rays emerge from the source, i.e., the focal spot, so that the radiation path from the source to each detector is the same, although other geometric arrangements and configurations have been suggested. See, for example, U.S. Pat. No. 5,668,851 entitled X-ray Tomography System With Stabilized Detector Response and issued on Sep. 16, 1997 in the name of John Dobbs; U.S. Pat. No. 5,757,878 entitled Improved Detector Arrangement For X-ray Tomography System and issued on May 26, 1998 in the names of John Dobbs and Ruvin Deych; U.S. Pat. No. 5,781,606 entitled X-ray Tomography System With Substantially Continuous Radiation Detection Zone and issued Jul. 14, 1998 in the names of John Dobbs and Ruvin Deych; and pending U.S. application Ser. No. 08/726638 entitled CT Scanner With Simulated Parallel Beam Design and filed in the United States Patent and Trademark Office on Oct. 7, 1996 in the names of John Dobbs and Ruvin Deych; all of these applications being assigned to the present assignee.

A Z-axis collimator is typically positioned between the X-ray source and the opening of the disk so that the thickness of the fan beam can be controlled in the Z-axis direction and so that the entire beam passing through the field of view (and any object disposed therein) is projected onto the detector array. The thickness of the beam defines the thickness of the slice through the object for which data is acquired. Until fairly recently, the detector array of a CT scanner of the third generation type has consisted of a single row of detectors. In order to generate sufficient data values to reconstruct an image of the portion of the object through which the beam passes, a typical array of the prior art type has had one row of detectors comprising approximately from 300 to 700 detectors, and either 1440 or 2880 projection views have been typically taken for a 360° scan. A machine of such design thus generates 432,000 to 2,016,000 data values per 360° scan. Until recently designing systems to generate more data values per scan was considered cost prohibitive because the detectors have represented a significant portion of the cost of the machine, and limitations have been imposed by the bandwidth of data acquisition systems and reconstruction computing systems for processing the data values.

However, with improvements in increased bandwidth of data acquisition systems and reconstruction computing systems and improvements in detector designs, machines have been developed with two dimensional (2D) detector arrays having multiple rows and columns of detectors. For example, the Elscint Twin CT scanner machine includes a detector array comprising two adjacent rows of detectors. The Z-axis thickness of the X-ray beam is set so that the beam projects onto both rows so that two slices can be simultaneously generated. With improved designs, cone beam systems for generating CT helical scans have become more practical. Such systems utilize a detector array comprising a plurality of rows of detector elements. See, for example, U.S. Pat. No. 5,262,946 entitled Dynamic Volume Scanning for CT Scanners and issued Nov. 16, 1993 to Huescher; U.S. Pat. No. 5,291,402 entitled Helical Scanning Computed Tomography Apparatus and issued on Mar. 1, 1994 to Armin H. Pfoh; U.S. Pat. No. 5,390,226 entitled Method and Apparatus for Pre-Processing Cone Beam Projection Data for Exact Three Dimensional Computer and issued Feb. 14, 1995 to Kwok C. Tam; U.S. Pat. No. 5,510,622 entitled X-ray Detector Array with Reduced Effective Pitch and issued Apr. 23, 1996 to Hui Hu et al; my copending application, now U.S. Pat. No. 5,818,897 entitled Quadrature Transverse CT Detection System and issued Oct. 6, 1998 to Bernard M. Gordon; and EP Published Patent Application, Publication No. EP 715830 published on Jun. 12, 1996, entitled Computerized Tomographic Scanners, and invented by Dale J. Bendula and Heang K. Tuy.

As shown in these references, 2D arrays comprising straight rows and columns of detector elements can be used, such as shown in the Pfoh, Huescher and Gordon patents, and the Bendula publication. Alternative arrangements are suggested in the Hu et al reference, wherein 2D arrays of detector elements are proposed in which the centers of the detector elements are aligned in one direction (either in the direction of the Z-axis or the direction coplanar with or parallel to the X-Y plane of the cone beam) so as to form either a plurality of parallel columns (when aligned in the direction of the Z-axis) as seen in FIGS. 3A, 3C and 3D of the reference; or a plurality of rows (when aligned in the direction of the X-Y planes) as seen in FIG. 3B of the reference. The detector elements however are alternately staggered in the other direction so that their centers are staggered. The Hu et al reference also suggests detector elements shaped as parallelograms so that their centers are aligned along rows and columns in two non-perpendicular directions. Such arrangements are provided to decrease the detector pitch along one or both dimensions of a 2D detector array, which is particularly useful for helical or volumetric scans.

In addition, the Gordon patent describes a 2D detector array comprising modules of two types of rectangularly shaped detector elements, one type having a longer dimension in the Z-axis direction, while the other type having a longer dimension in the direction within the X-Y plane. The latter detector elements are provided to insure detection of thin objects such as sheet explosives oriented parallel to the X-Y plane so as to insure detection.

With the ability to make 2D detector arrays and their use cost effective, machine designs are now being proposed to simultaneously provide multiple slices of the same thickness, and/or provide variable thickness slices. In one proposed design the 2D array comprises relatively small identically sized detector elements, each about 0.5 mm square, and arranged to form a 80 (elements per column) by 896 (elements per row) array. Multiple slices can be simultaneously generated, or variable thickness slices can be selectively generated, by using a corresponding set of select detector elements for each of the slices.

In this regard, a controllable switch is provided at the output of each detector element so that a detector element can be used to acquire data when the switch is on, and ignore any sensed data when the switch is off. All of the outputs of the detector elements of each column are summed together so that when a particular set of rows is switched on, the outputs of the switched detector elements of each column are summed together. In addition, the slice thickness is usually measured at the isocenter with the beam thickness actually being proportionally larger at the detector elements. However, for ease of exposition the slice thickness is described herein as the thickness of the beam portion projected onto the detector array.

Therefore, if a 3 mm slice is desired, the six rows of 0.5 mm square detector elements that are exposed to the beam are switched on, while the remaining elements are switched off. The six switched-on detector elements of each column can then be summed to provide one data value reading for each column for each projection view. Similarly, if multiple slices each of 3 mm are desired, adjacent groups of six rows of detector elements per group are simultaneously used (with the outputs of all of the switched-on detector elements of each column of each group being summed together) for the corresponding portions of the cone beam projected onto the groups of detector elements. In the example, when a 5.0 mm slice is required an adjacent group of ten rows are simultaneously used, with the outputs of the detector elements of each column of the group being switched on and summed together. Thus, any number of slice thicknesses in increments of 0.5 mm, can be provided by choosing the appropriate number of rows of detector elements and summing the outputs of the chosen detector elements, with each row providing an incremental increase of 0.5 mm thickness.

2D arrays comprising these relatively small detector elements, e.g., 0.5 mm, however, exhibit X-ray conversion inefficiencies. More particularly, for slice thicknesses of 1.0 mm and larger, each of the plurality of data values provided at each projection angle is a function of the X-ray photons received and converted by the multiple detector elements constituting a column of switched-on detector elements. Because the efficiency of each detector element typically drops off at its edges, and because no detection occurs in spaces between detector elements, a significant portion of the entire detector area comprising those switched-on detector elements being used to make up each column for receiving X-ray photons does not convert X-ray photons efficiently. Further, image artifacts can result should a detector switch be defective for one or more of the detector elements being used to receive and convert X-ray photons. More specifically, the responses of the columns of switched-on detector elements of each group, connected to provide a summed signal, will not be uniform and thus image artifacts may be created in the reconstructed image.

Accordingly, there is a need for an improved detector arrangement for acquiring CT data for variable thickness slices, and/or for multiple CT slices, and which reduces or overcomes these prior art problems.

SUMMARY OF THE INVENTION

The invention relates to a CT scanner system and a method. The system comprises a spatially encoded detector arrangement. The spatially encoded detector arrangement is designed so as to allow for more efficient detection areas for slices of various thicknesses, and preferably one or more sets of simultaneously generated multiple slices. By spatially encoding the array in accordance with a predetermined sequence code, the number of detector elements can be reduced from an array made of detector elements of equal length, and more efficient X-ray conversion achieved.

In accordance with one aspect of the invention, the CT scanner system comprises:
  a source of X-rays mounted for rotation about a Z-axis; and
  a plurality of detector elements arranged in a plurality of columns and positioned relative to the source and one another so that data values representative of CT slices of different thicknesses can be generated in response to X-rays being projected by the source onto corresponding select ones of the detector elements as the source rotates about the Z-axis;
  wherein the detector elements are sized and arranged so that at least some of the detector elements provided in each of the columns have lengths that vary in the Z-axis direction in accordance with a predetermined sequence code that represents all of the whole integer values in equal incremental values from 1 to N, wherein N is a whole integer greater than 1.

In accordance with another aspect of the invention, the CT scanner system comprises:
  a source of X-rays mounted for rotation about a Z-axis; and
  a plurality of detector elements positioned relative to the source and one another so that data values representative of any one of a plurality of CT slices of N different thicknesses can be generated in response to X-rays being projected by the source onto corresponding select ones of the detector elements as a function of the thickness of the CT slice, as the source rotates about the Z-axis;
  wherein the detector elements are sized and arranged in a spatially encoded arrangement so that multiple detector elements are provided in each of a plurality of columns disposed in the Z-axis direction with lengths that vary in the Z-axis direction such that the total number of detector elements for each column required to provide all of the CT slices of N different thickness is less than N, and N is an integer greater than 1.

In accordance with yet another aspect of the invention, the CT scanner system comprises:

a source of X-rays for selectively producing X-ray beams of various thicknesses mounted for rotation about a Z-axis, and a spatially encoded detector arrangement for use with any of the beams;

wherein the thickness of the beams vary in equal incremental amounts, and the spatially encoded detector arrangement comprises a plurality of detector elements arranged in a plurality of columns, each column including detector elements of two or more different lengths in the Z-axis direction arranged in a predetermined sequence so that each of the beams of various thicknesses can be projected onto select detector elements of each column having a detection area substantially matched to the thickness of the corresponding beam.

In one embodiment, N is greater than 3 requiring detector elements of at least three different lengths.

In one embodiment, the predetermined sequence code includes a biquinary code, or the sequence 5, 2, 2, 1. Other sequence codes can be used.

In one embodiment of the system the detection areas of the detector elements of at least some of the rows are dimensioned in the Z-axis direction such that multiple slices can be simultaneously generated by the system. The thicknesses of the multiple slices can be equal. The detection areas of the detector elements of at least some of the rows can be dimensioned in the Z-axis direction such that one of at least two different sets of multiple slices can be simultaneously generated by the system. The thicknesses of the multiple slices within each set can be equal, wherein the thickness of each of the slices of one set is different from the thickness of each of the slices of any other set.

The detector elements of at least one row each can have a length of "t", and the detector elements of at least one other row each can have a length of "2t". In addition, the detector elements of at least one other row each can have a length of "5t". The lengths of the detector elements of the rows can be arranged so as to be symmetrical about a line extending through the columns in a plane normal to the Z-axis. The length of the detector elements in the Z-axis direction can stay the same or increase with increasing distance from the line.

Various slice thicknesses can be provided by controlling the thickness of the X-ray beam in the Z-axis direction so that it only projects on those detector elements used to provide data values associated with the corresponding slices. Alternatively, the individual slices can be generated by using only the data values acquired from the detector elements associated with each slice.

In one preferred embodiment the array includes at least four rows of lengths "5t", "2t", "2t", "t" in sequential order, and in another preferred embodiment the array includes at least eight rows of lengths "5t", "2t", "2t", "t", "t", "2t", "2t" and "5t" in sequential order.

In accordance with another aspect a method of spatially encoding the detector elements of a CT scanner detector arrangement is described. The arrangement has a plurality of columns of the detector elements, each column arranged in a predetermined direction and the detector elements are sized and arranged so that data values representative of CT slices of different thicknesses can be generated between a minimum value and a maximum value. The method comprises:

distributing the detector elements of each column so that the lengths of at least some of the detector elements of each of the columns vary in accordance with a predetermined sequence code that represents all of the whole integer values in equal increments from 1 to N, wherein N is a whole integer greater than 1.

In one embodiment, the detector elements are of at least three different lengths and N is greater than 3.

In one embodiment the code is a biquinary code, and in particular includes the sequence 5, 2, 2, 1.

In one embodiment the step of distributing the detector elements can include:

varying the lengths of at least some of the detector elements so that one or more adjacent detector elements of each column can be combined to provide the appropriate detection area for the corresponding CT slices of different thicknesses.

In one embodiment the step of distributing the detector elements can include:

varying the lengths of at least some of the detector elements so that one or more adjacent detector elements of each column can be combined to the appropriate detection area for at least set of adjacent multiple slices of equal thicknesses simultaneously created by projecting a beam onto the detection elements.

In one embodiment the step of distributing the detector elements includes:

varying the lengths of at least some of the detector elements so that one or more adjacent detector element of each column can be combined to the appropriate detection area for any one of a plurality of sets of adjacent multiple slices simultaneously created by projecting a beam onto the detector elements, wherein the slices within each set are of equal thickness, and the thickness of the slices of one set differ from the slices of the other sets.

In one embodiment the step of distributing the detector elements includes the step of distributing at least some of the detector elements so that the lengths of the detector elements stay the same or increase with increasing distance from the center line of each column.

In one embodiment the step of distributing the detector elements includes the step of distributing at least some of the detector elements in rows such that the lengths of the detector elements of at least one row is equal to t, and the lengths of each of the detector elements of at least one other row is equal to 2t.

In one embodiment the step of distributing the detector elements includes the step of further distributing the detector elements so that the lengths of each of the detector elements of at least one other row is equal to 5t.

BRIEF DESCRIPTION OF THE DRAWINGS

The foregoing and other objects of this invention, the various features thereof, as well as the invention itself, may be more fully understood from the following description, when read together with the accompanying drawings in which.

DETAILED DESCRIPTION OF THE INVENTION

Figure 1:
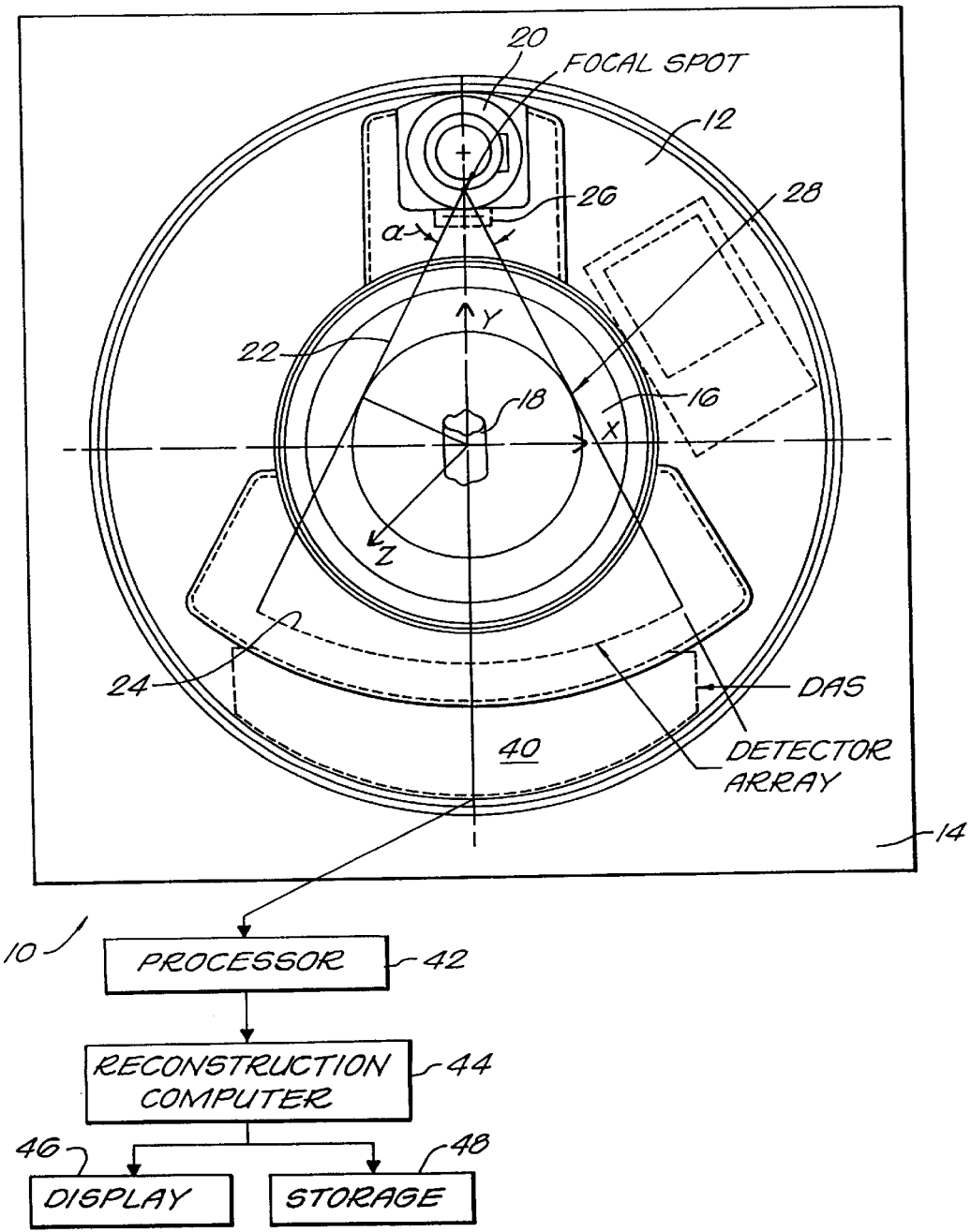
FIG. 1 is an end view of a CT scanner of the type embodying the present invention.
Figure 2:
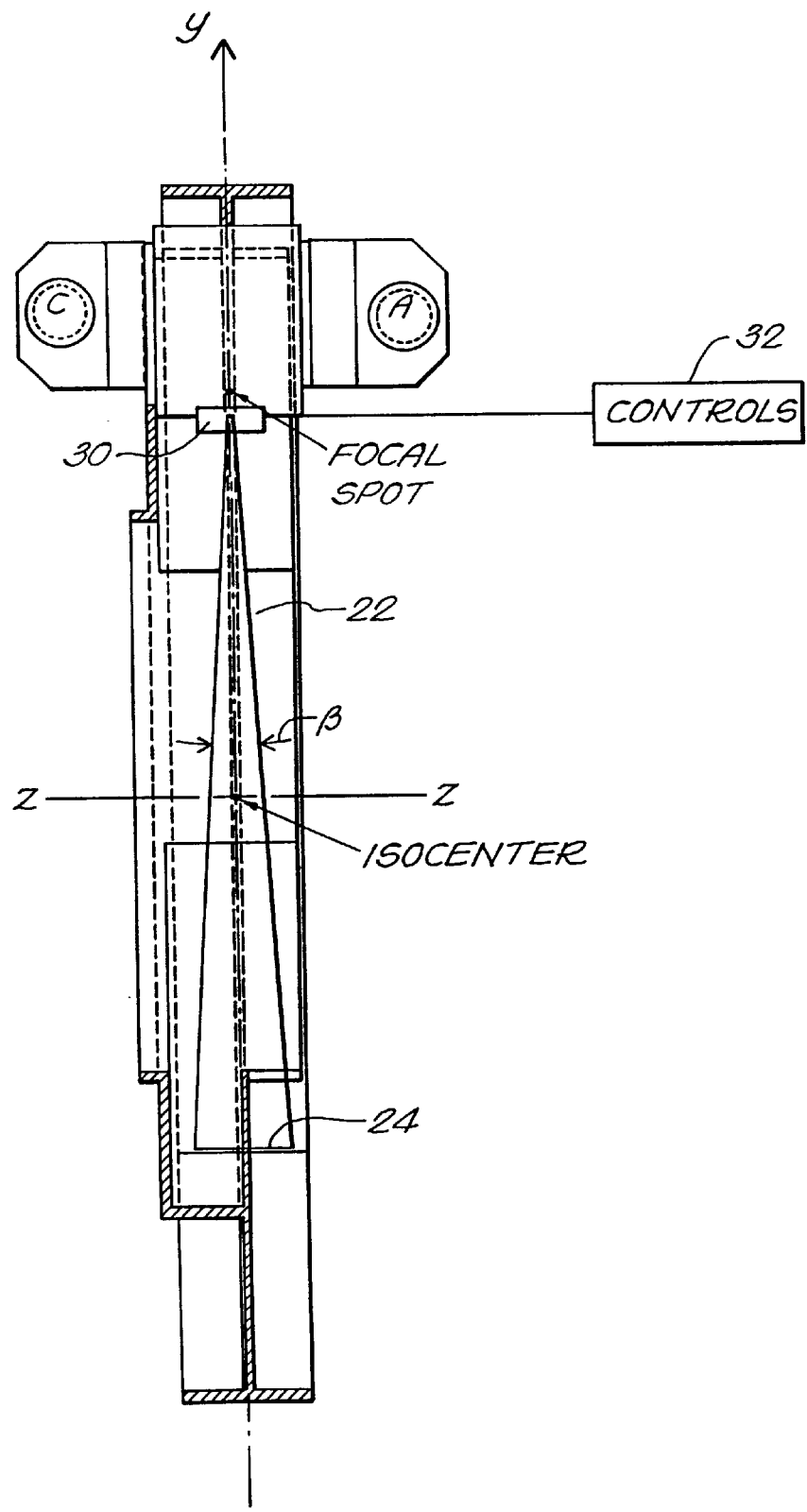
FIG. 2 is a cross-sectional view taken along line 1—1 of FIG. 1.

Referring to FIGS. 1 and 2, CT scanner 10 includes a disk or platform 12 rotatably supported within a gantry support 14 about the rotation axis, indicated as the Z-axis. The disk is provided with an opening 16 for receiving an object 18, which is the subject of the scan. The object, for example, can be a live subject in which case the scanner is classified as a medical scanner. However, the scanner has other uses including the detection of explosives and other contraband. An X-ray source 20 is positioned on the disk for generating an X-ray cone beam 22 across the opening 16 so as to pass through the object 18 before being projected onto the detector array 24 positioned on the platform diametrically opposite the source 20. As shown the shape of the beam is defined by two collimators, and X-Y plane collimator, indicated at 26 in FIG. 1, for controlling the cone beam angle (α) of the cone beam within and parallel to the X-Y plane (a plane disposed normal to the Z-axis), and in part defining the reconstruction circle or field of view 28. The Z-axis collimator, indicated at 30 in FIG. 2 controls the cone beam angle (β) in the Z-axis direction. In the illustrated embodiment, the Z-axis collimator is operable in response to an operator command through controls 32 for controlling the aperture of the Z-axis collimator. Controls 32 allow the operator to control the thickness of the cone beam 22 so that the latter is of a thickness in the Z-axis direction selected from a predetermined number of select values, between a minimum and a maximum, examples of which will be described in greater detail hereinafter. These beam thicknesses are each a function of the slice thickness provided by the beam during a CT scan.

As shown in FIG. 1, the output of each of the detector elements of the detector array 24 is provided to a data acquisition system (DAS) 40, which in turn is connected to a processor 42. The latter provides the data values to the reconstruction computer 44 for use in reconstructing an image of a portion of the object 18 which is exposed to the X-ray beam 22, the image being further processed, for example, for display (as seen at 46), or for storage (as seen at 48). The detector array 24 preferably includes a plurality of detector elements arranged in a two dimensional array of columns, each disposed in the direction of the Z-axis, and rows, each disposed in a plane transverse to the Z-axis. In this connection the detector elements can be designed as rectangular or square detector elements arranged in straight rows and columns. However, it should be understood that unless stated otherwise, the terms "rows" and "columns" as used herein should not be construed to be limited to detector elements having their geometric centers aligned in two mutually perpendicular directions, but can include detector elements having a staggered arrangement, as well as detector elements having other than a square geometric shape, such as the rectangular shaped detector elements shown in FIGS. 4–9 hereinafter, or the staggered and parallelogram approaches suggested in the Hu et al patent, referenced above.

In accordance with one aspect of the present invention, the length in the Z-axis direction of the detector elements of each column varies in accordance with a predetermined sequence code. Thus, in a 2D detector array arrangement, the length of the detector elements in the Z-axis direction of at least one row differs from the length of the detector elements in the Z-axis direction of at least one adjacent row so that a different group of select rows of detector elements are correspondingly used with each of the different beams which vary in thickness in equal incremental amounts between minimum and maximum values. In accordance with one aspect of the invention the detector elements are sized and disposed so that each of the beams of various thicknesses each can be projected onto detector elements having a detection area substantially matched to the thickness of the corresponding beam. In accordance with another aspect, the detector array is also designed so that it is capable of generating simultaneous data values representing multiple slices from the cone beam projected onto the array during a scan. In one embodiment, the multiple slices of a set are all of the same thickness, and the thickness of the set of multiple slices can be preselected from two or more values.

Figure 3:
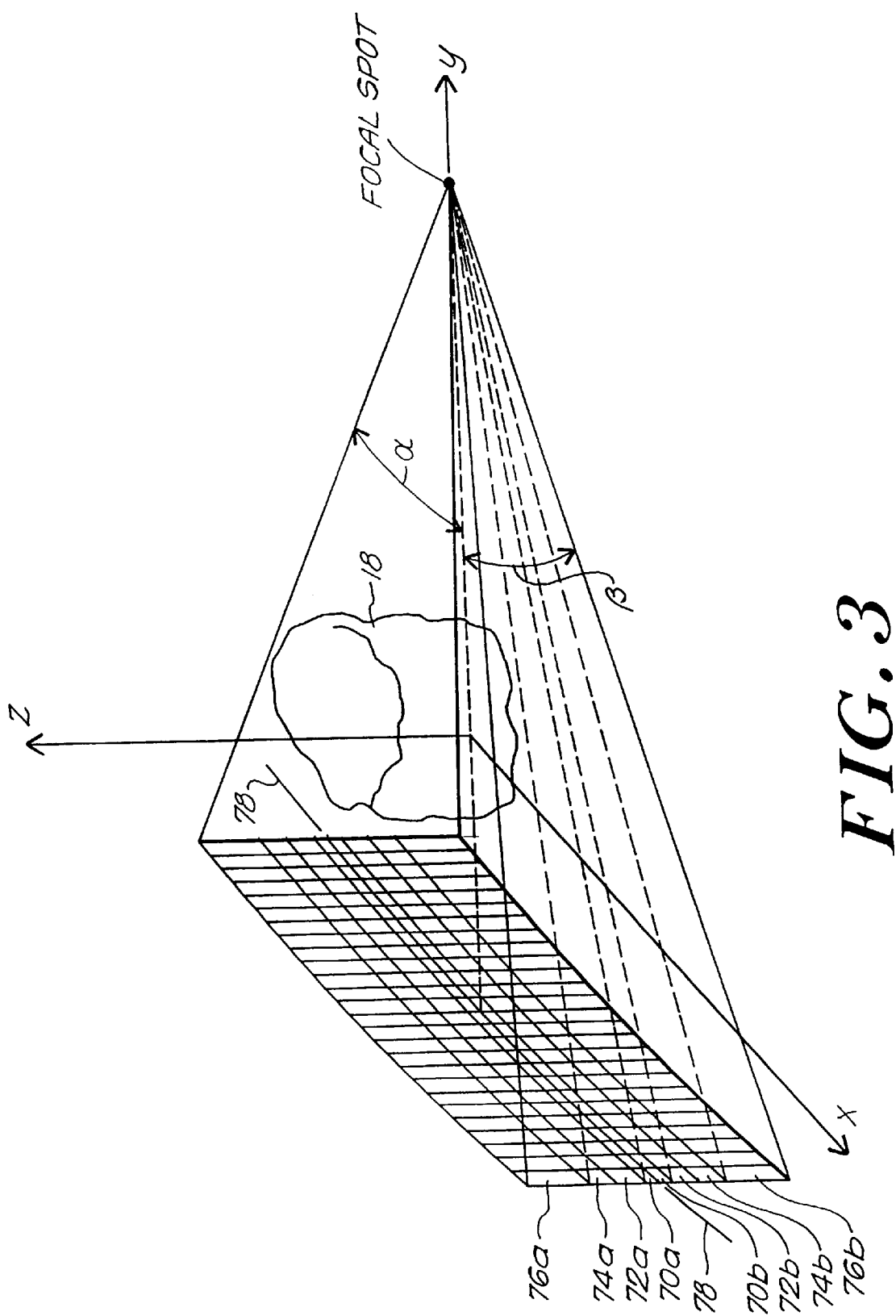
FIG. 3 is an isometric view of a preferred embodiment of the source and the detector array made in accordance with the present invention.

In one embodiment, as shown in FIG. 3, the illustrated sequence code includes what is referred to as a "biquinary" code. The "5, 2, 2, 1 "biquinary code sequence is a type of numerical code that can provide the sequence of all of the whole integer numbers from 1 to 10 while only using the four different coded values 5, 2, 2, 1. Thus, one is provided, two is provided, three can be obtained by adding one and two, four can be obtained by adding two and two, five can be provided by using the five, or adding two, two and one, six can be provided by adding five and one, and so forth. An added constraint is provided in the context of varying the length of the detector elements of each column in the Z-axis direction in accordance with a sequence code so that slices of different thickness can be provided in equal incremental amounts from "1t" to "10t". Specifically, providing CT slices whose thickness vary in equal increments from "1t" to "10t", requires that the corresponding beams be projected on either a single detection element in each column, or a combination of adjacent detector elements in each column. Thus, where the minimum slice thickness is "1t", selectively exposing the four rows could not achieve all of the ten different slices from "1t" to "10t", since, for example, the row of detector elements having a length "t" is not adjacent the row of detector elements having a length "5t", thus making it impossible to provide a slice thickness of "6t" using only the four rows. However, by adding an additional sequence of four detector elements symmetrically about the first four detector elements for each column so as to provide a sequence of "5t", "2t", "2t", "1t", "1t", "2t", "2t" and "5t", any where from one to eight adjacent rows of properly spatially encoded detector elements can provide matching detection areas for various CT slice thicknesses between "t" and "20t", including all of the CT slice thicknesses between "t" and "10t".

Figure 4:
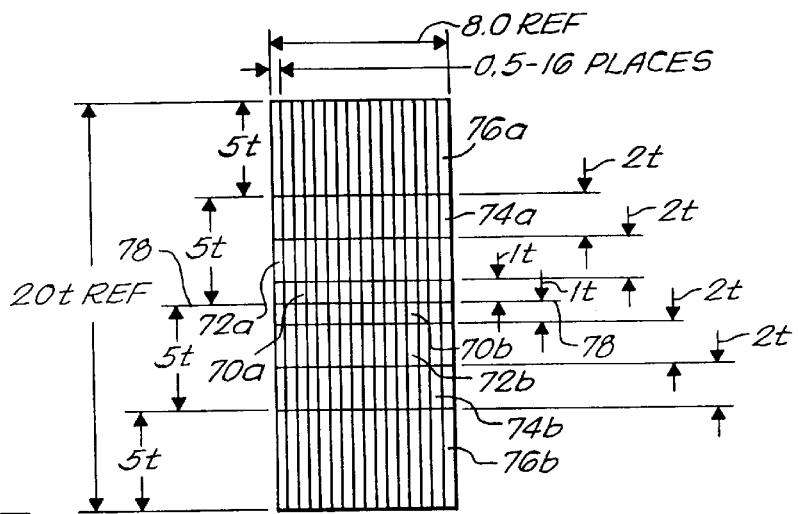
FIG. 4 is a top view of a section of the detector array shown in FIG. 3.

More particularly, by using a set of four adjacent rows 70a, 72a, 74a and 76a of lengths "t", "2t", "2t" and "5t", respectively, with a second set of identical rows 70b, 72b, 74b and 76b symmetrically arranged about the line 78 (as seen in FIGS. 3 and 4 as a center line between the eight rows) with the first set of adjacent rows, detection areas can be provided for any one of a plurality of slices of various thicknesses, from "1t" to "10t", and including additional values up to "20t". In fact the arrangement provides 14 different values with the use of only eight detector element rows. As seen in the following table, the output of one or the combined output of a plurality of adjacent detector elements can be used to generate the data values representative of the corresponding slice thicknesses:

TABLE I

| Slice thickness | Row selection(s) |
| --- | --- |
| t | 70 (a or b) |
| 2t | 70 (a & b) or 72 (a or b) or 74 (a or b) |
| 3t | [70 & 72] (a or b) |
| 4t | [72 & 74] (a or b), 70 (a & b) & [74a or 74b] |
| 5t | 76 (a or b), [70 & 72 & 74] (a or b) |
| 6t | 70 (a & b) & [72 & 74 (a or b)] |
| 7t | [74 & 76] (a or b) |
| 8t | 70 (a & b) & [72 (a & b)] & [74 (a or b)] |
| 9t | [72 & 74 & 76] (a or b) |
| 10t | [70 & 72 & 74 & 76] (a or b) |
| 11t | [70 & 72 & 74 & 76] (a or b) & 70 (b or a) |
| 12t | |
| 13t | [70 & 72 & 74 & 76] (a or b) & [70 & 72] (b or a) |
| 14t | |
| 15t | [70 & 72 & 74 & 76] (a or b) & [70 & 72 & 74] (b or a) |
| 16t | |
| 17t | |
| 18t | |
| 19t | |
| 20t | [70 & 72 & 74 & 76] (a and b) |

In the table, a row (or a bracketed set of rows) followed by the parenthetical "(a and b)" means those designated detector element rows appearing in the "a" set as well as the same designated detector element rows in the "b" set. A row (or a bracketed set of rows) followed by the parenthetical "(a or b)" means those designated detector element rows appearing in the "a" set or the same designated detector element rows in the "b" set. A first bracketed set of rows referring to "(a or b)" followed by a second set of rows referring to "(b or a)" means that where the first set of rows is selected from the "a" set, the second set of rows is selected form the "b" set, and vice versa.

Figures 5A, 5B, 5C, 5D, 5E:
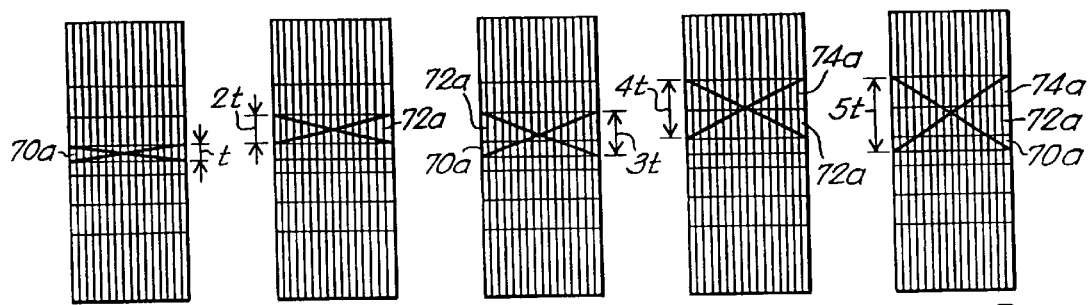
FIGS. 5A–5M show the how the various combinations of detector elements of the section of the detector array shown in FIG. 4 are used to provide data values corresponding to the various slice thicknesses.
Figures 5F, 5G, 5H, 5I, 5J:
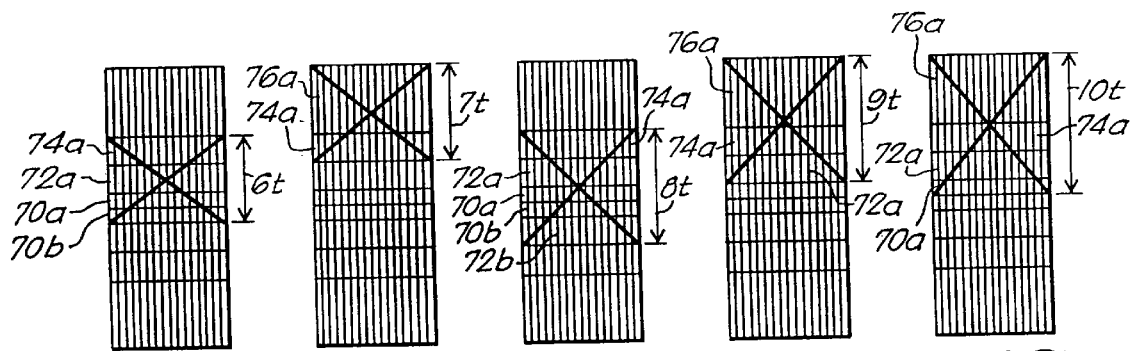
Figures 5K, 5L, 5M, 5N:
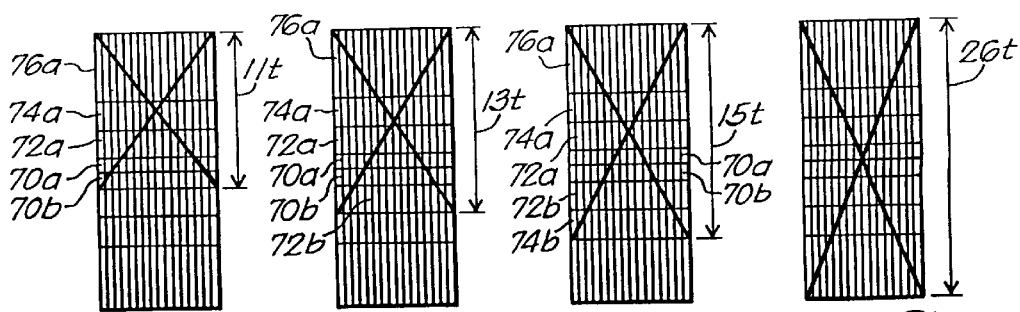

Examples of each of the detector element combinations and how the corresponding beam is projected onto the particular combination of detector elements are shown in FIGS. 5A–5N.

Figure 6:
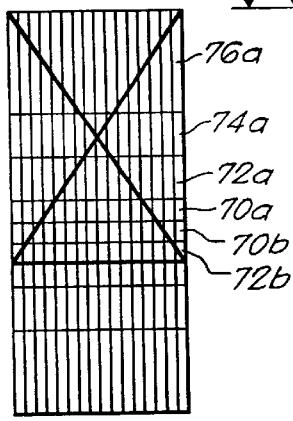
FIG. 6 shows a modification of the use of the embodiment shown in FIG. 4.
Figure 7:
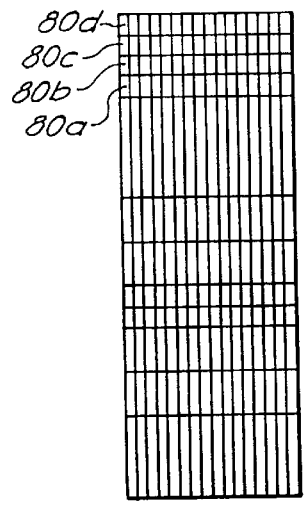
FIG. 7 shows another embodiment of the detector array.
Figure 8:
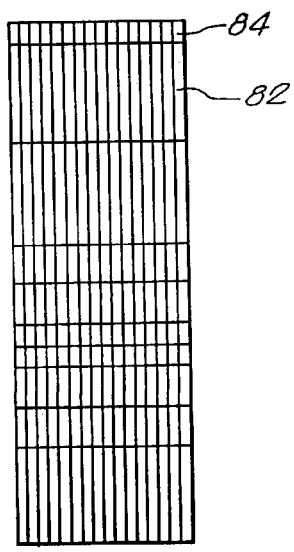
FIG. 8 shows yet another embodiment of the detector array.

As can be seen by the table above, a combination of rows of detector elements are provided for most values of n, where the thickness of slice is defined by "nt", wherein n is an integer from 1 to 20. The only values not provided with this particular spatial encoding arrangement of 5-2-2-1-1-2-2-5, are the values for 12t, 14t, 16t, 17t, 18t and 19t. These values can be obtained by using a part of an adjacent row to detect the X-ray photons. For example, for the slice having a thickness of 12t, the beam can be projected onto rows 76a, 74a, 72a, 70a, 70b and half of row 72b, as illustrated in FIG. 6, by using the Z-axis collimator to limit the thickness of the beam in the Z-axis direction so that the beam is projected only onto the area therein defined. Similarly, arrangements using a part of a detector element row can be made for the other values 14t, 16t, 17t, 18t and 19t. Alternatively, up to four rows of detector elements of length t can be added to either end of the detector element arrangement as shown by rows 80a, 80b, 80c and 80d shown in FIG. 7, or two additional rows of length "5t" and "t", respectively, can be added as shown as rows 82 and 84 in FIG. 8. However, in many practical applications, such as medical CT scanners, providing every value of n for "nt" may not be necessary. For example, for most body parts the following slice thicknesses may be satisfactory: 0.5 mm, 1.0 mm, 2.0 mm, 3.0 mm, 5.0 mm, 7.5 mm and 10.0 mm. In such a case t would equal 0.5 mm, and from the table it can be seen that all of the values are satisfied (t, 2t, 4t, 6t, 10t, 15t and 20t). In such a scanner it may be satisfactory to use the 5-2-2-1-1-2-2-5 arrangement.

Figure 9:
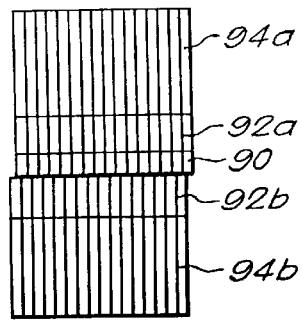
FIG. 9 shows still another embodiment of the detector array.

It will be evident that other arrangements can be used. For example, if a scanner only required to produce data values representative of "t", "2t", "3t", "5t", "7t" and "10t" thickness slices, where for example t=1 mm, a simple 5-2-1-2-5 arrangement can be used as shown in FIG. 9. In this case the following table shows the combination of detector elements used for each slice thickness.

TABLE II

| Slice thickness | Row selection(s) |
| --- | --- |
| t | 90 |
| 2t | 92a or 92b |
| 3t | 90 & 92 (a or b) |
| 5t | 94 (a or b) or [90 & 92] (a & b) |
| 7t | [92 & 94] (a & b) |
| 10t | [90 & 92 (a & b)] & 94 (a or b) |

Thus, in accordance with one aspect of the invention the specific spatial encoding employed does not need to necessarily include combinations of row selections for every increment of n, only those values of n that are desired.

In addition, depending upon the specific arrangement selected, preferably the spatially encoded detector array should also accommodate multiple slices taken simultaneously by projecting the cone beam, or a part of the cone beam, onto multiple groupings of rows of detector elements. For example, the 5-2-2-1-1-2-2-5 arrangement shown in FIG. 4, can provide from two up to four slices, each "5t" thick since each row 76 provides a "5t" slice, and each combination of rows 70, 72 and 74 provide a "5t" slice. Thus, multiple slices can be processed at the same time by selecting and processing data values detected by the following groups of rows of detector elements:

TABLE III

| Number of 5t slices | Row selection(s) |
| --- | --- |
| two | [70 & 72 & 74 & 76] (a or b) or [70 & 72 & 74] (a and b) |
| three | [70 & 72 & 74] (a and b) & 76 (a or b) |
| four | all rows |

Depending on the specific spatial encoding, the thickness of the set of multiple slices can be selected from a group of more than one different thickness. For example, in addition to the a set of up to four "5t" slices that can be simultaneously obtained with the arrangement shown in FIG. 4, a set of two multiple slices of "4t" thickness, a set of two multiple slices of "3t" thickness, a set of two to five multiple slices of "2t" thickness and a set of two multiple slices of "1t" can each be obtained.

As shown, a "4t" slice can be obtained by either pair of rows 72a and 74a, or the pair of rows 72b and 74b, while the other "4t" slice is obtained by the combination of rows 70a and 70b, and either row 72a or 72b (the row not used with the other "4t" slice). A "3t" slice is obtained by each group of combined rows of 70a and 72a, and combined rows 70b and 72b. "2t" slices can be simultaneously obtained by each row 72a, 72b, 74a and 74b, and the combined rows 70a and 70b. Similarly, two slices of thickness "1t" can be simultaneously obtained by each of the rows 70a and 70b.

It should be appreciated that for each set, one or two additional slices of equal thickness can be simultaneously generated with each of the "4t", "3t", "2t" and "1t" sets by using a part of one or two rows to detect the X-ray photons. For example, the set of "4t" slices can be increased from two up to four slices, each "4t" thick, by using the remaining row 74a or 74b (not used to generate the first two slices "4t" thick) together with a part of the row 76a or 76b adjacent thereto. The part of the row that is used is of a length "2t" adjacent to the selected row 76. The remaining row 74a or 74b (providing a length of "2t") and the part (of length "2t") of row 76 adjacent thereto provide the detection area for one additional slice of "4t" thick. The other "4t" slice can be provided by projecting the beam on a part of the other row 76 not used with the other slices, adjacent to a row 74 that is used. The part of the row 76 used is of a length of "4t".

In a similar manner, the set of "3t" slices can be increased from two up to four slices, each "3t" thick by using the detector elements of row 74a combined with a part of detector elements of row 76a and the detector elements of row 74b combined with a part of detector elements of row 76b (the part of the detector elements of rows 76a and 76b which are "1t" in length adjacent to the detector elements of rows 74a and 74b). "2t" thick slices can be increased from five up to seven slices, each of "2t" thick, by using a part of each of the detector elements of rows 76a and 76b (the part of the detector elements which are 2t in length adjacent to the detector elements of rows 74a and 74b). Finally, the set of "1t" slices can be increased from two up to four slices, each of "1t" thick, by using a part of each of the detector elements of rows 72a and 72b (the part of the detector elements which are "1t" in length adjacent to the detector elements of rows 72a and 72b).

Projecting X-rays onto a portion of one or more rows of the detector arrangement can be accomplished by using the Z-axis collimator to limit the thickness of the beam in the Z-axis direction so that it is projected onto the detection area therein defined.

Thus, by providing a spatially encoded detector arrangement, with columns of different lengths, the different slice thickness can be achieved in an efficient manner to allow for variable slice thicknesses and multiple slices for CT scanning.

Figure 10:
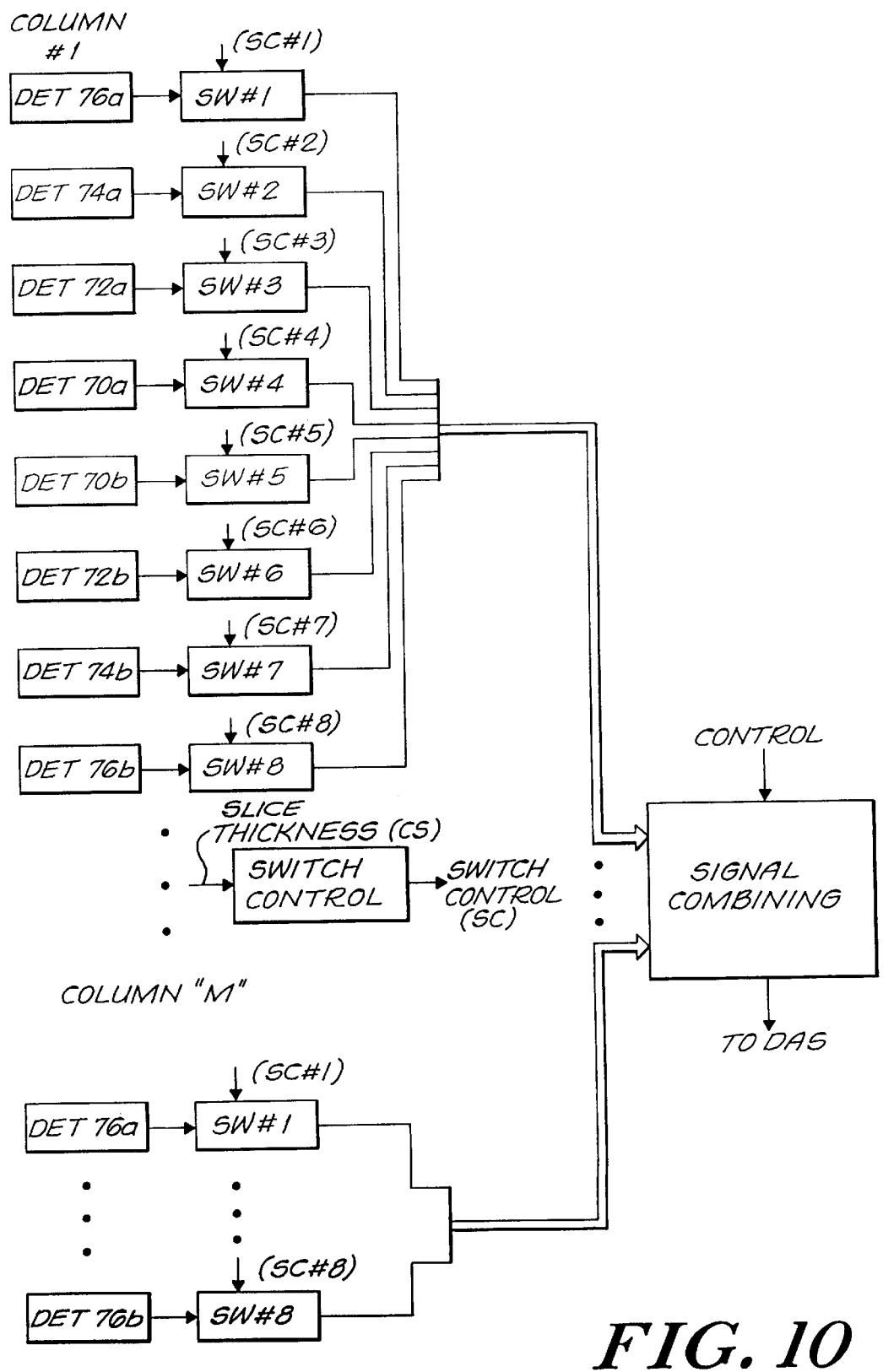
FIG. 10 shows a block diagram of one method of acquiring data using the detector array shown in FIGS. 3 and 4.

As shown in FIG. 10, in one embodiment the outputs of the detector elements forming each column are connected to corresponding switches. By opening and closing the switches with the switch controller, one can control which outputs are provided to the signal combiner. Thus, for single slices the switch controller determines which detector elements of each column represent the detection area for each data value generated at each projection angle of a scan. Thus, if the detector elements of row 70a are used to provide a slice thickness of "t", the switch controller closes all of the switches controlling the output of each detector element of the row 70a for each column. Where multiple slices of equal thickness are generated, the switch controller closes the appropriate switches, and the signal combiner combines the signals in the predetermined manner so as to achieve data values representative of the multiple slices.

It should be appreciated, that the slice thickness of each variable thickness slice and the combined thickness of multiple slices can be determined by the Z-axis collimator 30 and which of the switches for each column are closed. In this regard, where slices are generated based upon the entire detector area of one or more detector elements, the Z-axis collimator can be set to a maximum thickness so as to project onto the entire array, and the slice thickness controlled solely by the switch controller, by solely controlling the thickness of the beam. However, by using both, the slice thickness is can be controlled to a greater degree (since parts of the detection area of detector elements can be exposed as described above) and the radiation exposure is reduced to the level necessary for a particular scan.

Where switches are used, the advantage of the present design is that the number of switches per column is greatly reduced from that provided, for example, with a detector array, using square elements used to achieve the same results. Further, by using the sequence coding of varying lengths greater X-ray conversion efficiency is achieved over those 2D arrangements using an array of uniformly sized detector elements.

While the embodiments have been described in the context of third generation machines, the invention can also be used in fourth generation machine designs. In fourth generation machine designs the detectors are typically positioned stationary on the gantry support 14 at equal angular incremental positions. The source 20 rotates with the platform 12 so that the beam is projected toward the various detectors as the platform rotates about the Z-axis. In accordance with one aspect of the invention the detector elements would be provided on the gantry support 14 as columns substantially parallel to the Z-axis at the corresponding incremental positions with the corresponding like detector elements of the columns aligned in planes normal to the rotation axis.

The invention may be embodied in other specific forms without departing from the spirit or essential characteristics thereof. The present embodiments are therefore to be considered in respects as illustrative and not restrictive, the scope of the invention being indicated by the appended claims rather than by the foregoing description, and all changes which come within the meaning and range of the equivalency of the claims are therefore intended to be embraced therein.

What is claimed is:

1. A CT scanner system comprising:

a source of X-rays mounted for rotation about a Z-axis; and a plurality of detector elements arranged in a plurality of columns and positioned relative to the source and one another so that data values representative of CT slices of different thicknesses can be generated in response to X-rays being projected by the source onto corresponding select ones of the detector elements as the source rotates about the Z-axis wherein the detector elements are sized and arranged so that at least some of the detector elements provided in each of the columns have lengths that vary in the Z-axis direction in accordance with a predetermined sequence code that includes the sequence of 5, 2, 2, 1, 1, 2, 2, 5 and represents all of the whole integers in equal incremental values from 1 to at least 10; and an apertured device for defining a beam of X-rays emanating from the source and directed onto select ones of the detector elements, the apertured device being adjustable in the Z-axis direction so that the thickness of the beam can be controlled so as to generate X-rays from the source only toward the select ones of the detector elements having detection areas substantially matched to the thickness of the corresponding beam.

2. A CT scanner system according to claim 1, wherein the detector elements of each column required to represent the sequence code is less than 10.

3. A CT scanner system according to claim 1, wherein the lengths of the detector elements are sized and arranged in accordance with the predetermined sequence code so that data values representative of at least one set of a plurality of CT slices of equal thicknesses can be simultaneously generated.

4. A CT scanner system according to claim 1, wherein the lengths of the detector elements are sized and arranged in accordance with the predetermined sequence code so that data values representative of any one of a plurality of sets of CT slices can be simultaneously generated, wherein the CT slices within each set are of equal thickness and different from the thickness of the slices within each other set.

5. A CT scanner system according to claim 1, wherein each of the detector elements provides an output as a function of X-rays detected by said detector element, and only the outputs of the corresponding select ones of the detector elements are processed for generating each slice of selected thickness.

6. A CT scanner system according to claim 1, wherein the detector elements are arranged in a 2D array of rows and columns.

7. A method of spatially encoding the detector elements of and using the detector elements in a CT scanner detector arrangement having a plurality of columns of the detector elements oriented in the Z-axis, each column arranged in a predetermined direction and the detector elements being sized and arranged so that data values representative of CT slices of different thicknesses can be generated between a minimum value and a maximum value, comprising:

distributing the detector elements of each column so that the lengths of at least some of the detector elements of each of the columns vary in accordance with a predetermined sequence code that includes 5, 2, 2, 1, 1, 2, 2, 5 and represents all of the whole integer values in equal increments from 1 to at least 10;

adjusting an apertured device for defining a beam of X-rays emanating from the source that are directed to select ones of the detector elements, the apertured device being adjustable in the Z-axis direction so that the thickness of the beam can be controlled so as to generate X-rays from the source only toward the select ones of the detector elements having detection areas substantially matched to the thickness of the corresponding beam.

8. A method according to claim 7, wherein the step of distributing the detector elements includes:

varying the lengths of at least some of the detector elements so that one or more adjacent detectors of each column can be combined to provide the appropriate detection area for the corresponding CT slices of different thicknesses.

9. A method according to claim 7, wherein the step of distributing the defector elements includes:

varying the lengths of at least some of the detector elements so that one or more adjacent detector of each column can be combined to the appropriate detection area for at least a set of adjacent multiple slices of equal thicknesses simultaneously created by projecting a beam onto the detection elements.

10. A method according to claim 7, wherein the step of distributing the detector elements includes:

varying the lengths of at least some of the detector elements so that one or more adjacent detector of each column can be combined to the appropriate detection area for any one of a plurality of sets of adjacent multiple slices simultaneously created by projecting a beam onto the elements, wherein the slices within each set are of equal thickness, and the thickness of the slices of one set differ from the slices of the other sets.

* * * * *

UNITED STATES PATENT AND TRADEMARK OFFICE
CERTIFICATE OF CORRECTION

PATENT NO. : 6,188,745 B1
DATED : February 13, 2001
INVENTOR(S) : Bernard M. Gordon It is certified that error appears in the above-identified patent and that said Letters Patent is hereby corrected as shown below:

Claim 9, column 14,
Line 21, delete "defector" and insert therefor -- detector --.

Signed and Sealed this

Twenty-fifth Day of September, 2001

Attest:

*Nicholas P. Godici*

NICHOLAS P. GODICI
*Attesting Officer*    *Acting Director of the United States Patent and Trademark Office*